United States Patent [19]

Drewlow

[11] Patent Number: Plant 6,297

[45] Date of Patent: Sep. 20, 1988

[54] IMPATIENS PLANT NAMED EQUINOX

[75] Inventor: Lyndon W. Drewlow, Ashtabula, Ohio

[73] Assignee: Mikkelsens, Inc., Ashtabula, Ohio

[21] Appl. No.: 916,560

[22] Filed: Oct. 8, 1986

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Schwartz, Jeffery, Schwaab, Mack, Blumenthal & Evans

[57] ABSTRACT

An impatiens plant named Equinox, having light pink flowers, with magenta eyes; dark purplish green foliage; self-branching and floriferous habit, and having the ability to tolerate both high and low temperatures.

1 Drawing Sheet

The present invention relates to a new and distinctive cultivar of impatiens plant, botanically known as Impatiens, and referred to by the cultivar name Equinox. Equinox was developed by me through controlled breeding by crossing Mikkelsen Seedling No. 83-749-1 (seed parent) with Mikkelsen Seedling No. 83-726-7 (pollen parent). Asexual reproduction of the progeny of the stated cross by terminal or stem cuttings performed in Ashtabula, Ohio has shown that unique features of this new impatiens are stabilized and are reproduced true to type in successive propagations.

The following characteristics in combination distinguish the new impatiens from both its parent varieties and other cultivated impatiens of this type known and used in the floriculture industry. In certain instances the characteristics are compared with similar characteristics of other cultivars. Of the cultivars referred to, Dawn is disclosed in U.S. Plant Pat. No. 5,775; Eclipse is disclosed in U.S. Plant Pat. No. 4,689; Columbia is disclosed in U.S. Plant Pat. No. 5,126; and Aurora and Zenith are disclosed in pending applications.

1. Equinox is a larger plant than Dawn and Aurora, more mounded than Columbia, and similar in size and shape to Zenith.

2. Equinox is lighter pink in flower color than Aurora, Dawn and Columbia. Equinox has a distinct magenta eye that extends to the lower areas of the petals except for the upper petal which is similar to the eye of Aurora. Columbia has a small area of magenta at the center of the flower, and Dawn has a whitish area at the center of the flower.

3. The flowers of Equinox are larger than Dawn, similar in size to Aurora and Columbia, but not as large as the flowers on Zenith. Petals overlap resulting in an almost circular flower.

4. Leaf color is similar to Eclipse including the red venation. However, Eclipse has no variegations while Equinox has some cream variegation at the base of the leaf under high light conditions. Equinox has more red in the leaf than Aurora which is dark green with cream variegation. Dawn and Columbia are both bright green leaved with cream variegation.

5. Equinox has shown tolerance to high temperatures and sunlight without getting burn on the foliage.

6. Equinox has a leaf that is similar in shape and size to Aurora, Columbia and Zenith, while Dawn has a smaller leaf and Eclipse a narrower leaf.

7. Flowering of Equinox is 7 to 10 days earlier than Eclipse, and similar to Dawn, Aurora, Columbia and Zenith.

8. Equinox is highly self-branched and floriferous, with the flowers being carried above the foliage thereby making Equinox suited for 4"-6" pots and hanging basket use.

9. Leaf margin of Equinox is entire with fine cilia, similar to Aurora, while Columbia and Dawn have finely serrated leaves with fine cilia.

10. Equinox shows average to good ability to continue to flower under low light and 70° F. temperature without fading or flower size reduction. By contrast, the flowers on Columbia fade and become smaller in size, and Dawn does not continue to flower.

The accompanying colored photograph illustrates in perspective the overall appearance of Equinox, showing the colors as true as it reasonably possible to obtain in a colored reproduction of this type. It should be noted in this regard that the overall color in the photograph appears somewhat lighter than the main petal color, the stated value for which is accurate.

The following is a detailed description of my new impatiens cultivar based on plants produced under commercial practices in Ashtabula, Ohio both under greenhouse and outdoor conditions. The photograph was taken in June from plants grown under greenhouse conditions. Color references are made to the Royal Horticultural Society Colour Chart except where general terms of ordinary dictionarysignificance are used.

Parentage: A controlled cross between Mikkelsen Seedling No. 83-749-1 with Mikkelsen Seedling No. 83-726-7.

Propagation:

(A) *Type cutting.*—Stem cutting 15 mm long will develop to 4 to 5 cm long in 18 to 21 days.

(B) *Time to root.*—8 to 10 days at 23° C. summer, and 10 to 12 days at 20° C. winter.

(C) *Rooting habit.*—Heavy, fibrous.

Plant description:

(A) *Form.*—Symmetrically mounded, compact, self-branching, red stemmed, vigorous growing, flowering herb.

(B) *Habit of growth.*—Compact, self-branching, mounded, flowering over the top of the foliage, continuous flowering, vigorous.

(C) *Foliage description.*—Broad reddish green leaves with red venation and a trace of cream variegation at the base of some leaves under high light conditions. (1) Size: 14 to 16 cm long and 3 to 4 cm wide at maturity. Environment can affect the size of the leaf. (2) Shape: Lanceolate with acuminate apex and acute base. (3) Texture: Upper rugose, lower glabrous. (4) Margin: Entire and finely ciliated. (5) Color: Young foliage top side 146B, tinged with 183B. Under side: 183B. Mature foliage top side 146A, tinged with 183A. Under side: 183A. (6) Venation: Pinnate, reddish purple in color.

Flowering description:

(A) *Flowering habits.*—Flowers continuously from leaf whorl in progressively orderly manner with usually one flower per leaf axil, but on occasion there may be two. Whorl above starts to open about the time the last axil on the whorl below flowers. Takes 5 to 7 days from bud to bloom, and flowers last 2 to 3 weeks depending on the environment.

(B) *Natural flowering season.*—Indeterminant and continuous. Quantity of flowering increases with increasing levels of light.

(C) *Flower buds.*—Ellipsoidal, flowers perfect, reddish spur up to 3.5 cm long on mature bud with throat behind ovary and originating from the major sepal.

(D) *Flowers borne.*—On individual short pedicels from whorl of 4 to 5 leaves flowering progressively around the whorl as buds and leaves develop. Most leaf axils have only one flower but occasionaly there will be two.

(E) *Quantity of flowers.*—Quite floriferous; flowering development is continous so that tight buds to mature blooms are visible at the same time in large numbers.

(F) *Petals.*—(1) Shape: Heart shaped with upper petal dominant in size. (2) Color: Top side in summer when opening 36C tinged with 85C and with a 67A eye, fading to 36D; under side 85C with 67A line down center of each petal except the upper petal which is mostly that color on the back side. (3) Number of petals: Five (5) in number. (4) Size of flowers: 5.5 to 6.0 cm.

(G) *Reproductive organs.*—(1) Stamens: Five (5) number. (a) Anther shape: Hooded, color cream with reddish cast. (b) Pollen color: Cream. (2) Pistels (a) Stigma: Five (5) in number, segmented column shaped, color reddish tinge. (b) Style color: Reddish tinge. (c) Ovaries: Five (5) in number, size 4 mm, color green with a purple cast near tip.

Disease resistance: No significant disease or insect problems noted to date.

SUMMARY OF IMPORTANT CHARACTERISTICS OF NEW CULTIVAR

1. Contrast between the light pink flowers with magenta eye and the dark purplish green foliage.
2. Ability to tolerate low temperatures (40°-50° F.) both in the spring and fall which extends the flowering season.
3. Numerous cuttings produced on each plant which makes propagation easy.
4. Floriferous nature which makes it an excellent pot and hanging basket plant.

I claim:

1. A new and distinct cultivar of impatiens plant named Equinox, as described and illustrated, and particularly characterized by its light pink flowers, with magenta eyes; dark purplish green foliage; self-branching and floriferous habit, and by its ability to tolerate both high and low temperatures.

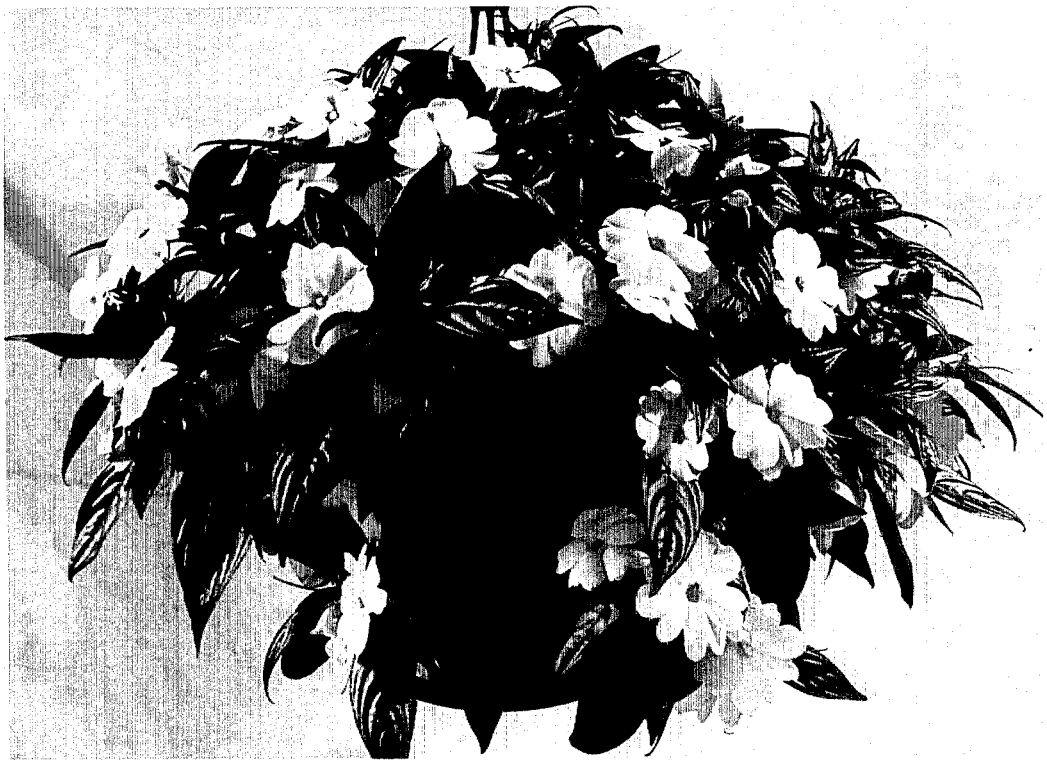

* * * * *